US008852097B2

(12) United States Patent
Shimada et al.

(10) Patent No.: US 8,852,097 B2
(45) Date of Patent: Oct. 7, 2014

(54) METABOLIC ENERGY MONITORING SYSTEM

(75) Inventors: Kazuyuki Shimada, Saitama (JP); Hiroyuki Kuriyama, Kawasaki (JP); Hideyuki Ban, Kodaira (JP)

(73) Assignee: Hitachi, Ltd., Tokyo (JP)

( * ) Notice: Subject to any disclaimer, the term of this patent is extended or adjusted under 35 U.S.C. 154(b) by 970 days.

(21) Appl. No.: 11/806,241

(22) Filed: May 30, 2007

(65) Prior Publication Data

US 2007/0282176 A1    Dec. 6, 2007

(30) Foreign Application Priority Data

Jun. 2, 2006 (JP) ................................. 2006-154167

(51) Int. Cl.
*A61B 5/00* (2006.01)
*A61B 5/024* (2006.01)
*G06F 19/00* (2011.01)
*A61B 5/01* (2006.01)

(52) U.S. Cl.
CPC ........ *A61B 5/02438* (2013.01); *G06F 19/3406* (2013.01); *A61B 5/01* (2013.01); *A61B 2562/0219* (2013.01)
USPC .......................................... 600/301; 600/300

(58) Field of Classification Search
None
See application file for complete search history.

(56) References Cited

U.S. PATENT DOCUMENTS

| | | | | |
|---|---|---|---|---|
| 6,095,949 | A * | 8/2000 | Arai ................................... | 482/4 |
| 6,478,736 | B1 * | 11/2002 | Mault ............................ | 600/300 |
| 6,547,727 | B1 * | 4/2003 | Hashiguchi et al. ........... | 600/300 |
| 6,595,929 | B2 * | 7/2003 | Stivoric et al. ................ | 600/549 |
| 6,694,182 | B1 * | 2/2004 | Yamazaki et al. ............. | 600/547 |
| 6,790,178 | B1 * | 9/2004 | Mault et al. .................... | 600/300 |
| 6,834,436 | B2 * | 12/2004 | Townsend et al. .............. | 33/512 |
| 7,008,350 | B1 * | 3/2006 | Yamazaki et al. ................ | 482/8 |
| 7,020,508 | B2 * | 3/2006 | Stivoric et al. ................ | 600/390 |
| 7,054,756 | B2 * | 5/2006 | Shimada et al. ................ | 702/19 |
| 7,424,318 | B2 * | 9/2008 | Brister et al. ................. | 600/347 |

(Continued)

FOREIGN PATENT DOCUMENTS

| JP | 10-318779 | 5/1997 |
|---|---|---|
| JP | 2003-93372 | 9/2001 |

(Continued)

OTHER PUBLICATIONS

Office Action issued by the Japanese Patent Office on Aug. 23, 2011 in the corresponding Japanese Patent Application No. 2006-154167 (3 pages), along with an English language translation (2 pages).

*Primary Examiner* — Bill Thomson
*Assistant Examiner* — Bobby Soriano
(74) *Attorney, Agent, or Firm* — Nicholas Trenkle; Stites & Harbison, PLLC.

(57) ABSTRACT

A metabolic energy monitoring system is provided which comprises: a wearable device having a movement sensor, a temperature sensor and a pulse wave sensor and adapted to be worn on a human body; a database to store activity state decision knowledge data including activity state decision condition data and calorie consumption calculation knowledge data including a calorie consumption calculating algorithm for each metabolic state; an activity state decision unit to determine the activity state based on a detection signal from the wearable device and activity state decision knowledge data; a metabolic state decision unit to detect an activity continuation state, and determine the metabolic state; a calorie consumption calculating unit to calculate a calorie consumption according to the metabolic state; and an output unit to output the calorie consumption.

6 Claims, 11 Drawing Sheets

(56) References Cited

U.S. PATENT DOCUMENTS

| | | | |
|---|---|---|---|
| 2002/0019585 A1* | 2/2002 | Dickinson | 600/300 |
| 2002/0107433 A1* | 8/2002 | Mault | 600/300 |
| 2002/0109600 A1* | 8/2002 | Mault et al. | 340/573.1 |
| 2002/0156351 A1* | 10/2002 | Sagel | 600/300 |
| 2002/0164676 A1* | 11/2002 | Shimada et al. | 435/32 |
| 2002/0183646 A1* | 12/2002 | Stivoric et al. | 600/549 |
| 2003/0126593 A1* | 7/2003 | Mault | 725/10 |
| 2003/0130595 A1* | 7/2003 | Mault | 600/567 |
| 2003/0167188 A1* | 9/2003 | Hashiguchi et al. | 705/2 |
| 2003/0208110 A1* | 11/2003 | Mault et al. | 600/300 |
| 2003/0208113 A1* | 11/2003 | Mault et al. | 600/316 |
| 2004/0059202 A1* | 3/2004 | Mori | 600/300 |
| 2004/0117212 A1* | 6/2004 | Kong et al. | 705/2 |
| 2004/0133081 A1* | 7/2004 | Teller et al. | 600/300 |
| 2004/0152957 A1* | 8/2004 | Stivoric et al. | 600/300 |
| 2005/0113650 A1* | 5/2005 | Pacione et al. | 600/300 |
| 2006/0094938 A1* | 5/2006 | Shimada et al. | 600/301 |
| 2007/0051369 A1* | 3/2007 | Choi et al. | 128/204.21 |
| 2007/0106132 A1* | 5/2007 | Elhag et al. | 600/301 |
| 2007/0282176 A1* | 12/2007 | Shimada et al. | 600/300 |
| 2008/0033762 A1* | 2/2008 | Jung et al. | 705/3 |
| 2008/0033763 A1* | 2/2008 | Jung et al. | 705/3 |

FOREIGN PATENT DOCUMENTS

| | | |
|---|---|---|
| JP | 2003-093372 | 4/2003 |
| JP | 2005-115799 | 10/2003 |
| JP | 2005-230340 | 2/2004 |
| JP | 2006-075184 | 3/2006 |
| JP | 2006-129887 | 5/2006 |
| WO | WO 97/47239 | 6/1997 |

\* cited by examiner

FIG. 3

300 DATA ACCUMULATING DATABASE

310 USER DATA HISTORY TABLE

| 311 USER ID | 312 SD DATA | 313 ACTIVITY STATE ID | 314 METABOLIC STATE ID | 315 CALORIE CONSUMPTION | 316 DATE & TIME | |
|---|---|---|---|---|---|---|
| --- | --- | --- | --- | --- | --- | |
| user0001 | WD_ID=wd01,SD_ID=sd01,Ps=71,BT=36.0,Ac=50 | S_ST | M_ST | 1.05 | 2004/04/01 22:00 | ⟩310D |
| user0001 | WD_ID=wd01,SD_ID=sd01,Ps=82,BT=35.8,Ac=10 | S_SL | M_SL | 0.95 | 2004/04/01 22:01 | |
| --- | --- | --- | --- | --- | --- | |
| user0001 | WD_ID=wd01,SD_ID=sd01,Ps=62,BT=35.8,Ac=10 | S_SL | M_SL | 0.95 | 2004/04/02 06:00 | ⟩310E |
| user0001 | WD_ID=wd01,SD_ID=sd01,Ps=71,BT=36.2,Ac=50 | S_ST | M_ST | 1.05 | 2004/04/02 06:01 | |
| --- | --- | --- | --- | --- | --- | |
| user0001 | WD_ID=wd01,SD_ID=sd01,Ps=80,BT=36.2,Ac=210 | S_AC | M_AC | 3.15 | 2004/04/02 06:32 | ⟩310A |
| user0001 | WD_ID=wd01,SD_ID=sd01,Ps=80,BT=36.3,Ac=210 | S_AC | M_AC | 3.15 | 2004/04/02 06:33 | |
| --- | --- | --- | --- | --- | --- | |
| user0001 | WD_ID=wd01,SD_ID=sd01,Ps=80,BT=36.3,Ac=210 | S_AC | M_AC | 3.15 | 2004/04/02 07:00 | ⟩310F |
| user0001 | WD_ID=wd01,SD_ID=sd01,Ps=80,BT=37.3,Ac=50 | S_ST | M_AB | 3.15 | 2004/04/02 07:01 | ⟩310B |
| user0001 | WD_ID=wd01,SD_ID=sd01,Ps=78,BT=37.3,Ac=50 | S_ST | M_AB | 2.68 | 2004/04/02 07:02 | |
| --- | --- | --- | --- | --- | --- | |
| user0001 | WD_ID=wd01,SD_ID=sd01,Ps=72,BT=36.3,Ac=50 | S_ST | M_AB | 1.28 | 2004/04/02 08:00 | ⟩310C |
| user0001 | WD_ID=wd01,SD_ID=sd01,Ps=71,BT=36.2,Ac=50 | S_ST | M_ST | 1.05 | 2004/04/02 08:01 | |
| --- | --- | --- | --- | --- | --- | |
| user0001 | WD_ID=wd01,SD_ID=sd01,Ps=71,BT=36.2,Ac=50 | S_ST | M_ST | 1.05 | 2004/04/02 22:30 | |
| user0001 | WD_ID=wd01,SD_ID=sd01,Ps=62,BT=35.8,Ac=10 | S_SL | M_SL | 0.95 | 2004/04/02 22:31 | |
| --- | --- | --- | --- | --- | --- | |
| user0001 | WD_ID=wd01,SD_ID=sd01,Ps=62,BT=35.8,Ac=10 | S_SL | M_SL | 0.95 | 2004/04/03 07:01 | |

FIG. 11A  METABOLIC STATE WHEN RESTING
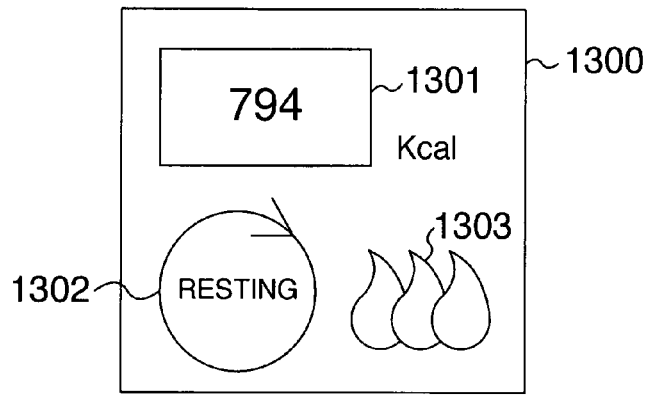
FIG. 11B  METABOLIC STATE WHEN ACTIVE
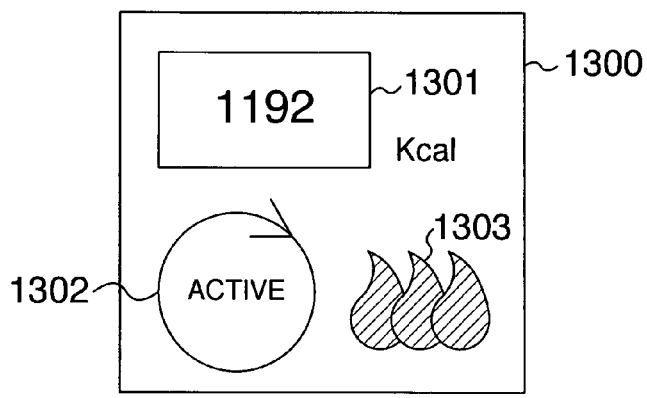
FIG. 11C  POST-ACTIVITY METABOLIC STATE
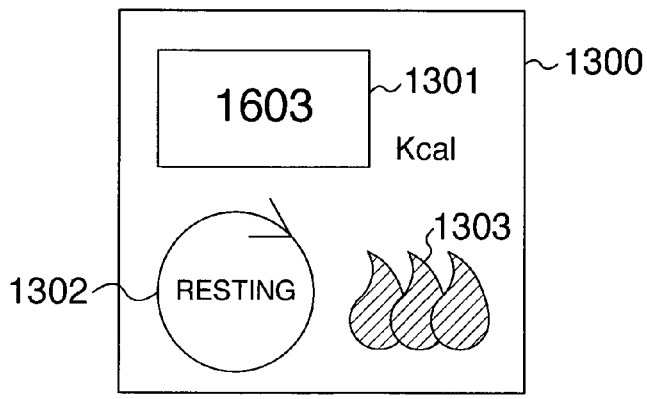

US 8,852,097 B2

METABOLIC ENERGY MONITORING SYSTEM

INCORPORATION BY REFERENCE

The present application claims priority from Japanese application JP 2006-154167 filed on Jun. 2, 2006, the content of which is hereby incorporated by reference into this application.

BACKGROUND OF THE INVENTION

The present invention relates to a wearable device and system to collect biological information of a user to monitor his or her metabolic state and calculate a calorie consumption.

As needs for enhancing health of middle-aged and elderly people and for preventing life-style related diseases have been growing in recent years, there is an increasing call for a user to be able to easily check his or her metabolic energy (energy consumption or calorie consumption) in a daily life for use in his routine health care.

For such a healthcare support, there has been a device that is worn by the user at all times to monitor a calorie consumption.

For example, an "energy consumption estimation device" described in JP-A-2005-230340 estimates an energy consumption (calorie consumption) from a walking speed and an inclination angle both calculated based on measurements of an acceleration sensor and an atmospheric pressure sensor.

As another example, an "activity level history storage device" in JP-A-10-318779 determines an amount of physical activity (calorie consumption) from an intensity of activity calculated from a movement detection signal.

Still another example includes a "calorie consumption measuring device" in JP-A-2003-93372 and WO1997/047239 which calculates a calorie consumption from a heart rate according to a regression equation when the user is at rest or exercising.

Further, a "health management system" described in JP-A-2005-115799 determines a state of activity from biological information obtained from sensors and changes a calculation process accordingly.

These conventional technologies, however, have a problem of not being able to determine the calorie consumption correctly because they do not consider a metabolism in a body. More specifically, in a recovery process following a physical activity of the user, the conventional technologies cannot detect a state in which the metabolism is at an elevated state (post-activity metabolic state), failing to calculate the calorie consumption with high precision.

SUMMARY OF THE INVENTION

An object of this invention is to provide a metabolic energy monitoring device and system which determines a metabolic state in a human body following physical activities and calculates a calorie consumption with high precision at all times.

The problem described above can be solved by a metabolic energy monitoring system which comprises: a wearable device having a movement sensor, a temperature sensor and a pulse wave sensor and adapted to be worn on a human body; a database to store activity state decision knowledge data and calorie consumption calculation knowledge data, the activity state decision knowledge data including activity state decision condition data, the calorie consumption calculation knowledge data including a calorie consumption calculating algorithm for each metabolic state; an activity state decision unit to determine the activity state based on a detection signal from the wearable device and activity state decision knowledge data; a metabolic state decision unit to detect an activity continuation state from the signal of the wearable device, wherein if an activity is found continuing, the metabolic state decision unit determines a metabolic state for each activity state, wherein if an activity is found not continuing, the metabolic state decision unit checks whether the metabolism is increasing; a calorie consumption calculating unit to calculate a calorie consumption by changing the calorie consumption calculating algorithm according to the metabolic state; and an output unit to output the calorie consumption.

With the metabolic energy monitoring device and system of this invention, the state of metabolism in the human body resulting from the body movements can be checked, allowing the calorie consumption to be calculated with high precision.

Therefore, the user can easily and accurately check his or her metabolism in the daily life and use it for health care, enhancement of health and prevention of life-style related diseases.

Other objects, features and advantages of the invention will become apparent from the following description of the embodiments of the invention taken in conjunction with the accompanying drawings.

BRIEF DESCRIPTION OF THE DRAWINGS

FIG. 3 is an example of a data accumulating database.

FIG. 11A is an example screen of an output unit of the wearable device.

FIG. 11B is an example screen of an output unit of the wearable device.

FIG. 11C is an example screen of an output unit of the wearable device.

DESCRIPTION OF THE INVENTION

Figure 1:
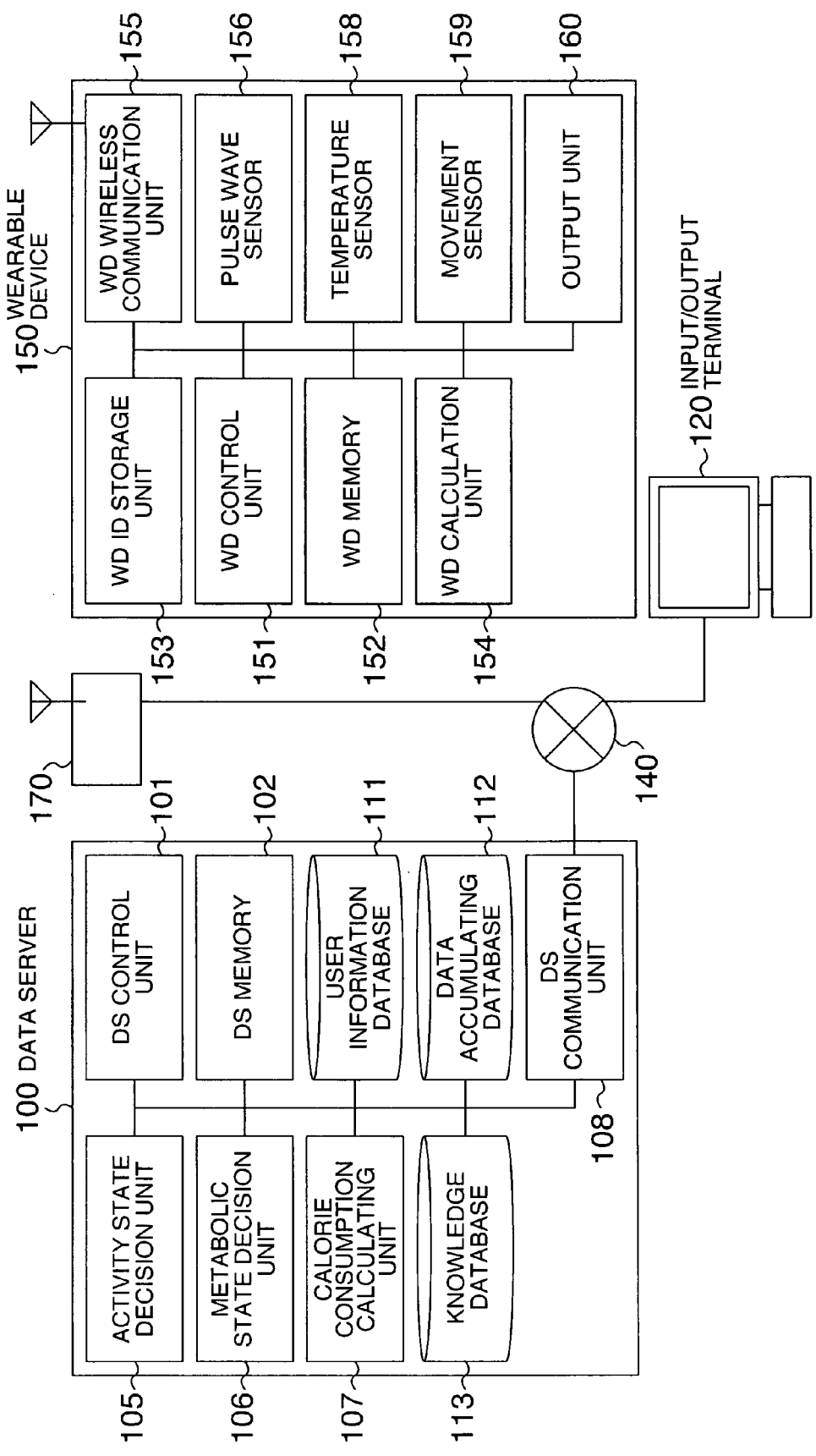
FIG. 1 shows a configuration of a metabolic energy monitoring device and system as one embodiment of this invention.

FIG. 1 shows a configuration of a metabolic energy monitoring device and system as one embodiment of this invention. This system comprises a data server 100, an input/output terminal 120, a network 140, a wearable device 150 and a wireless repeater 170.

In this embodiment, the input/output terminal 120 uses one or more personal computers having an input unit such as a keyboard and mouse, an output unit such as display, and a communication unit such as the data server 100. It is also possible to use a portable terminal, such as PDA, PHS and cell phone, having an input unit, an output unit and a communication unit.

This system has the home server 120 and the wireless repeater 170 installed in one of apartments of a collective housing such as condominium, with a dweller in the apartment (hereinafter referred to as a user) putting on the wearable device 150. The data server 100 is installed in a data center managed by a customer center, the operator of this system.

With the data server 100 installed in the data center, personal information of the user and privacy information such as biological data taken from the user can be managed in a unified manner, simplifying the security management such as prevention of information leaks.

The data server 100 can also be installed in a condominium, which in turn simplifies the building of the system.

Further, in this system the wireless repeater 170 may also be installed in a single-family house (simply referred to as a house or home) and the wearable device 150 worn by an occupant of the house (user). In this way the system can also be used in single-family houses.

The data server 100 comprises a DS control unit 101, a DS memory 102, an activity state decision unit 105, a metabolic state decision unit 106, a calorie consumption calculating unit 107, a DS communication unit 108, a user information database 111, a data accumulating database 112, and a knowledge base 113.

The wearable device 150 comprises a WD control unit 151, a WD memory 152, a WD_ID storage unit 153, a WD calculation unit 154, a WD wireless communication unit 155, a pulse wave sensor 156 to detect a change in blood flow in blood vessel caused by heart beat, a temperature sensor 158 to detect an amount of heat energy generated in the user's body, a movement sensor 159 to detect a physical activity as a body motion, and an output unit 160.

In this embodiment, "wd01" is stored in the WD_ID storage unit 153.

The wearable device 150 wirelessly communicates with the wireless repeater 170.

The wearable device 150 is built into a wrist band to be worn on a wrist of the user. It may also be incorporated into other articles worn on the user's body, such as a wrist watch, locker key, pendant, ring, clothes, shoes, hat and glasses. It can also be attached to an adhesive tape or compress which is then directly applied to a skin.

Figure 10:
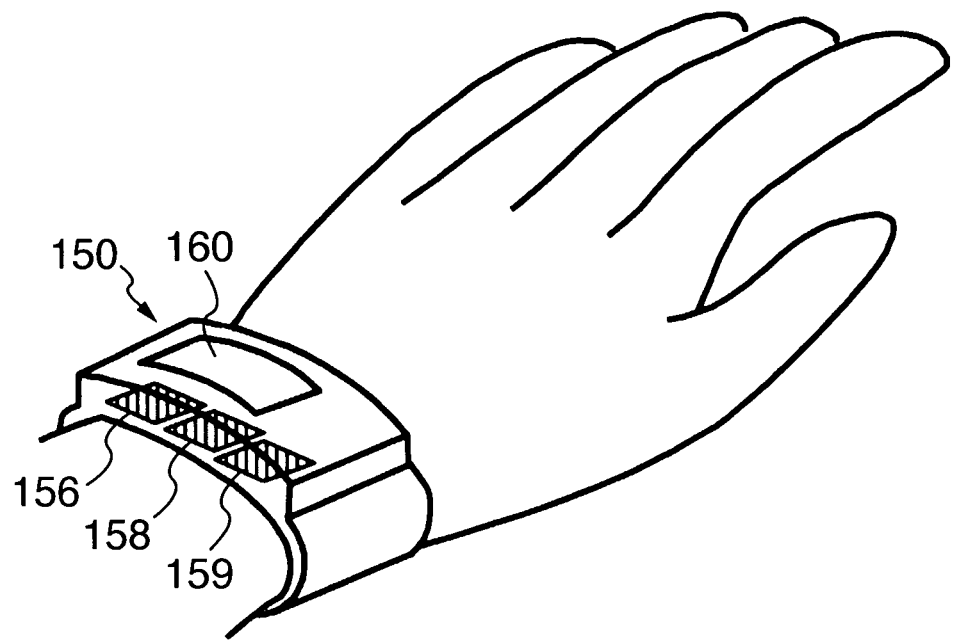
FIG. 10 is a schematic view showing the wearable device built into a wrist band.

FIG. 10 is a schematic view showing the wearable device 150 built into a wrist band. An arrangement is made to hold the pulse wave sensor 156 and the temperature sensor 158 close to or in contact with the skin of the user so that the pulse wave and skin temperature can be detected. The movement sensor 159 is incorporated into the wrist band so that it can detect movements in a direction parallel to the back of the hand. This allows efficient detection of the user's physical movement.

The movement sensor 159 may use an impact sensor to reduce a power consumption. The movement sensor 159 can also use an acceleration sensor, which allows highly precise detection of body movements.

The output unit 160 is contemplated to use a liquid crystal display. It may also use other types of display device.

The network 140 is connected with the data server 100, the terminal 120, and the wireless repeater 170. The data server 100 communicates with the terminal 120 and the wireless repeater 170 through the network 140.

The network 140 uses a wired communication through a LAN (Local Area Network) cable. It can also use a power line communication (PLC) and other wired communication, wireless communication such as IEEE802.11b, and other special forms of communication system.

The network 140 can also use other customer premises network such as private premises PHS, and wide area networks such as internet, VPN, cell phone communication network and PHS communication network.

Although this system is described as being built with hardware, a part of the functions of this system can be constructed by software.

A part of the functions of the data server may be incorporated into the wearable device. This allows calorie consumption to be calculated by only the wearable device.

Figure 2:
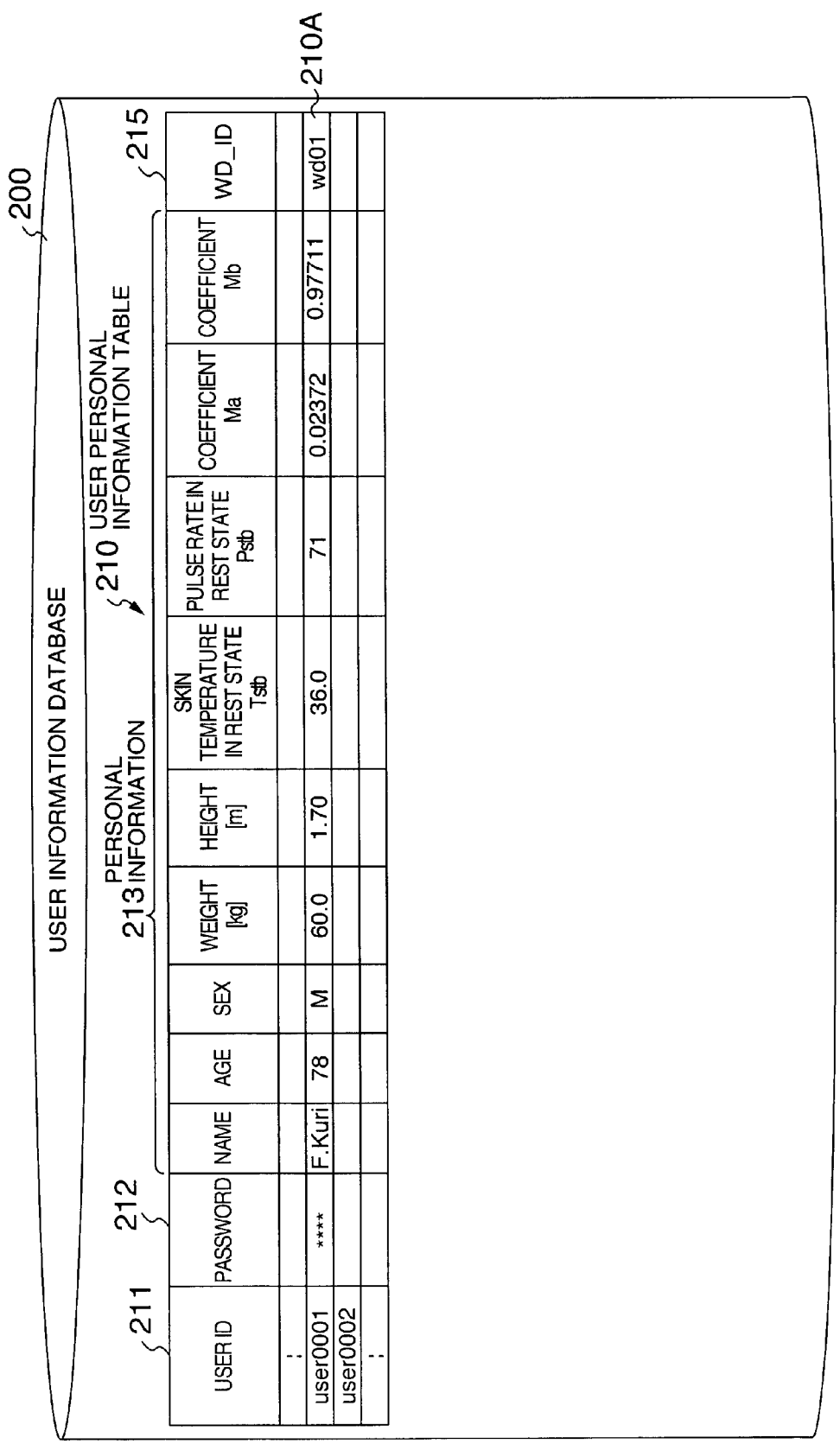
FIG. 2 is an example of a user information database.

FIG. 2 shows an example 200 of the user information database 111. The example database 200 comprises a user's personal information table 210 used to manage user's personal information. The user's personal information table 210 has a field 211 to store a user ID to identify the user, a field 212 to store a user password used to implement a user authentication when the user uses the system, a field 213 to store personal information such as name, and a field 215 to store WD_ID to identify the wearable device that the user wears. In a user's personal information record 210A of the table 210, for example, a user with user ID of "user0001" and name of "F. Kuri" uses a wearable device identified by WD_ID of "wd01".

FIG. 3 shows an example 300 of the data accumulating database 112. The data accumulating database 112 comprises a user data history table 310. The user data history table 310 has a field 311 to store the user ID, a field 312 to store SD data including user biological data sent from the wearable device 150, a field 313 to store an activity state ID identifying an activity state calculated from the user's biological data, a field 314 to store a metabolic state ID identifying a metabolic state calculated from the user's biological data, a field 315 to store a calorie consumption calculated from the user's biological data, and a field 316 to store date and time the SD data is received.

In this embodiment, the activity state ID of "S_SL" is defined to represent an activity state of "sleeping", the activity state ID of "S_ST" is defined to represent an activity state of "being at rest", and the activity state ID of "S_AC" is defined to represent an activity state of "being active".

Further, the metabolic state ID of "M_SL" is defined to represent a state of metabolism "when the user is sleeping", the metabolic state ID of "M_ST" is defined to represent a state of metabolism "when the user is resting", the metabolic state ID of "M_AC" is defined to represent a state of metabolism "when the user is actively moving", and the metabolic state ID of "M_AB" is defined to represent a state of metabolism "following activity".

Figure 4:
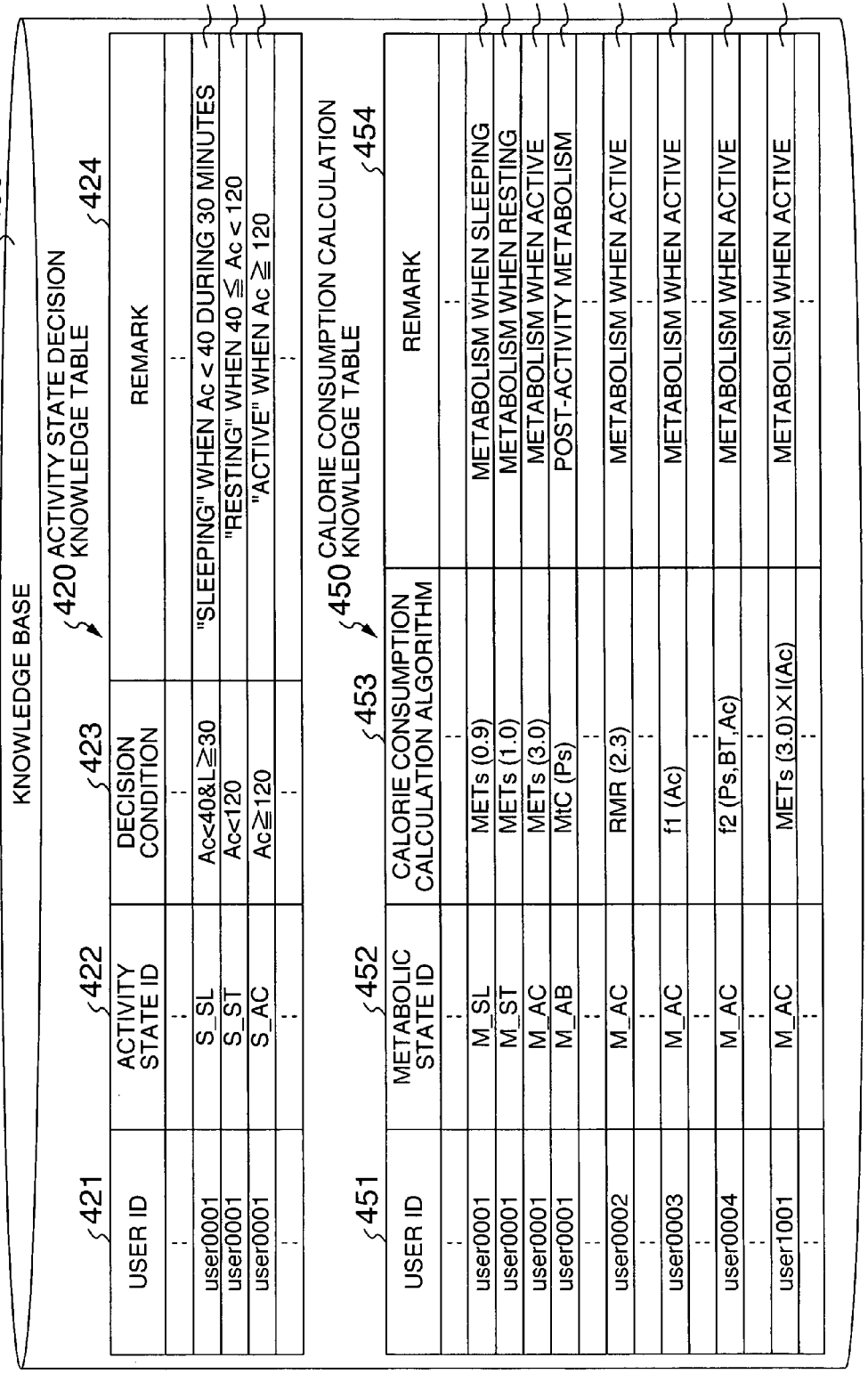
FIG. 4 is an example of a knowledge base.

FIG. 4 shows an example 400 of the knowledge base 113. The knowledge base 113 comprises an activity state decision knowledge table 420 to store knowledge based on which to make a decision on the activity state, and a calorie consumption calculation knowledge table 450.

The activity state decision knowledge table 420 comprises a field 421 to store the user ID, a field 422 to store an activity state ID, a field 423 to store a condition by which to make a decision on an activity state identified by the activity state ID, and a remark field 424.

In an activity state decision knowledge record 420C, for example, when the movement Ac of the user identified by the user ID "user0001" is 120 or more, the activity state is identified by the activity state ID of "S_AC", i.e., identified as "being active".

The calorie consumption calculation knowledge table 450 comprises a field 451 to store the user ID, a field 452 to store the metabolic state ID, a field 453 to store an algorithm for calculating a calorie consumption according to the metabolic state ID, and a remark field 454.

In the calorie consumption calculation knowledge record 450C, for example, when the metabolic state for a user identified by the user ID of "user0001" is "M_AC", i.e., the metabolic state is a "metabolism when a physical activity is active", the algorithm for calculating the calorie consumption is "METs(3.0)" indicating that an argument (METs value) in the calorie consumption calculating algorithm using METs is "3.0".

METs is an index representing a degree of metabolism for a particular level of physical activity as compared with a reference degree of metabolism when the physical activity is at rest. By using the METs value (unit: ml/kg/minute) defined for each level of physical activity (including exercise, work and routine activities) in an equation 1 defined below, a calorie consumption can be calculated (reference 1: Ainsworth B E, Haskell W L, Leon A S, et al. "Compendium of Physical Activities: classification of energy costs of human physical activities", Med Sci Sports Exerc. 1993 January; 25(1): 71-80)

$$METs\ (METs\ value) = OCI \times (OC \times METs\ value \times W \times T) / 1000 \qquad \text{Equation 1}$$

where OCI: coefficient converting 'amount of oxygen intake' into 'calorie consumption' [kcal/l]; OC: amount of oxygen intake when physical activity is at rest (1 MET) [ml/kg/min]; W: weight [kg]; and T: time [min].

Suppose, for example, OCI=5.0 [kcal/l] and OC=3.5 [ml/kg/min] when a user identified by the user ID of "user0001" is physically active. Using the weight W indicated in the parameter 213 of the user's personal information table 210, the calorie consumption in one minute is calculated to be $5.0 \times (3.5 \times 3.0 \times 60.0 \times 1)/1000 = 3.15$ [kcal].

Further, as in the case with a calorie consumption calculation knowledge record 450E, the calorie consumption can be calculated using the equation 1 and the amount of body movement Ac. For example, suppose Ac=280 when I(Ac)=Ac/210. The calorie consumption in one minute is METs $(3.0) \times I(280) = 4.20$ [kcal]. The use of the amount of body movement Ac allows the calculation of calorie consumption according to not only the state of physical activity but also the amount of body movement.

Further, as in the case with a calorie consumption calculation knowledge record 450D, the calorie consumption can also be calculated from pulses by a calorie consumption calculating algorithm "MtC(Ps)", as defined in equation 2. (Reference 2: Kazuyuki Kida, "Research into Estimation of Energy Consumption according to Heart Rate", Hirosaki Igaku Vol. 40, Number 1, 60-69, 1988).

$$MtC(Ps) = OCI \times (Ma \times Ps + Mb) \times T \qquad \text{Equation 2}$$

where OCI: coefficient converting 'amount of oxygen intake' into 'calorie consumption' [kcal/l]; Ps: pulse rate [times/min]; T: time [min]; and Ma, Mb: coefficients.

Suppose, for example, OCI=5.0 [kcal/l] when a user identified by the user ID of "user0001" is physically active and has a pulse rate of 80 times/min. Using the coefficients Ma, Mb described in the parameter 213 of the user's personal information table 210, the calorie consumption in one minute is calculated to be $5.0 \times (0.04667 \times 80 - 3.10333) \times 1 = 3.15$ [kcal].

The coefficients Ma and Mb can be calculated from the following simultaneous equations using metabolic energies and pulse rates before and after the post-activity metabolic state described later.

$$EE1 = OCI \times (Ma \times Ps1 + Mb) \times T$$

$$EE2 = OCI \times (Ma \times Ps2 + Mb) \times T$$

For example, consider a case in which immediately before the post-activity metabolic state, the metabolic energy EE1=3.15 and the pulse rate Ps1=80 (user data record 310F) and, after the post-activity metabolic state, the metabolic energy EE2=1.05 and the pulse rate Ps2=71 (user data record 310C). The above simultaneous equations result in Ma=0.04667 and Mb=3.10333.

By using the user data before and after the post-physical activity metabolic state in calculating the coefficients, as described above, it is possible to determine appropriate coefficients for a particular person and thereby improve the accuracy of calculation of calorie consumption.

As in a calorie consumption calculation knowledge record 450P, it is possible to use a calorie consumption calculating algorithm that uses a RMR (Relative Metabolic Rate).

It is also possible to use any desired equation as in the case with calorie consumption calculation knowledge records 450Q, 450R.

As described above, by storing the calorie consumption calculating algorithm in the knowledge base for each metabolic state, the calculation of calorie consumption can be set freely according to the metabolic state.

Next, an operation of this system will be explained with reference to the flow chart.

Figure 5:
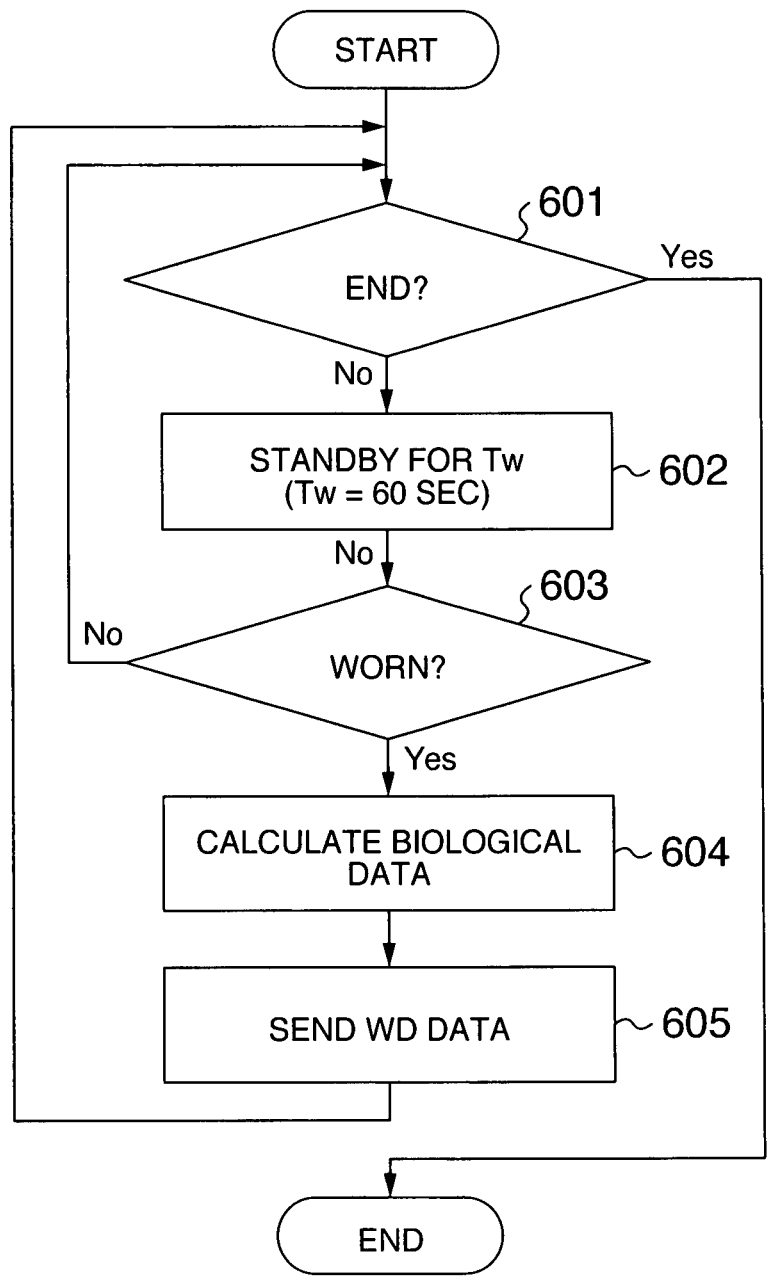
FIG. 5 is a flow chart showing an operation of a wearable device.

FIG. 5 shows a flow chart representing an operation of the wearable device 150. First, when the wearable device 150 starts its operation, the WD control unit 151 executes a step 601 to decide whether or not to exit the processing. If the step 601 decides that the processing should stop, this operation ends.

If the step 601 decides that the operation should not be stopped, the WD control unit 151 executes a step 602 of standing by for a standby time Tw. Although in this embodiment, the standby time Tw is set to "60 seconds", any arbitrary time may be used.

Next, at step 603 the WD control unit 151 checks whether the wearable device 150 is worn by the user. For example, when an output value of the pulse wave sensor 156 is smaller than a predetermined value, it is decided that the wearable device 150 is worn by the user. When an output value is greater than the predetermined value, it is decided that the wearable device 150 is not worn.

If at step 603 it is decided that the device is not worn, the WD control unit 151 executes the step 601 and the subsequent steps recursively.

If the step 603 decides that the device is worn, the WD control unit 151 starts the WD calculation unit to execute a step 604 that calculates as biological data a pulse rate Ps from the pulse wave sensor 156, a skin temperature BT from the temperature sensor 158 and a body movement Ac from the movement sensor 159. For example, the calculation of the pulse rate Ps involves calculating peak values from the pulse wave output from the pulse wave sensor 156 and counting the number of peaks in the past 60 seconds.

In calculating the skin temperature BT, a voltage value output from the temperature sensor 158 is converted into the skin temperature BT by using a conversion equation that converts the voltage value into the skin temperature.

In calculating the body movement Ac, the number of times that a scalar value representing the magnitude of the body movement output from the movement sensor 159 changes from below a predetermined value to above it and the number of times that the scalar value moves from above the predetermined value to below it are summed up as the body movement Ac.

The body movement Ac may also be calculated as a total of scalar values representing the magnitudes of movement output from the movement sensor 159.

Next, the WD control unit 151 starts the WD wireless communication unit 155 to execute a step 605 of transmitting the biological data calculated by the step 604 as the WD data, together with the WD_ID.

For example, if the biological data has a pulse rate Ps of "80", a skin temperature BT of "36.2" and a body movement Ac of "210", then "WD_ID=wd01, Ps=80, BT=36.2, Ac=210) (WDDATA01) is transmitted as the WD data.

The WD data transmitted by step 605 is received by the wireless repeater 170.

Figure 6:
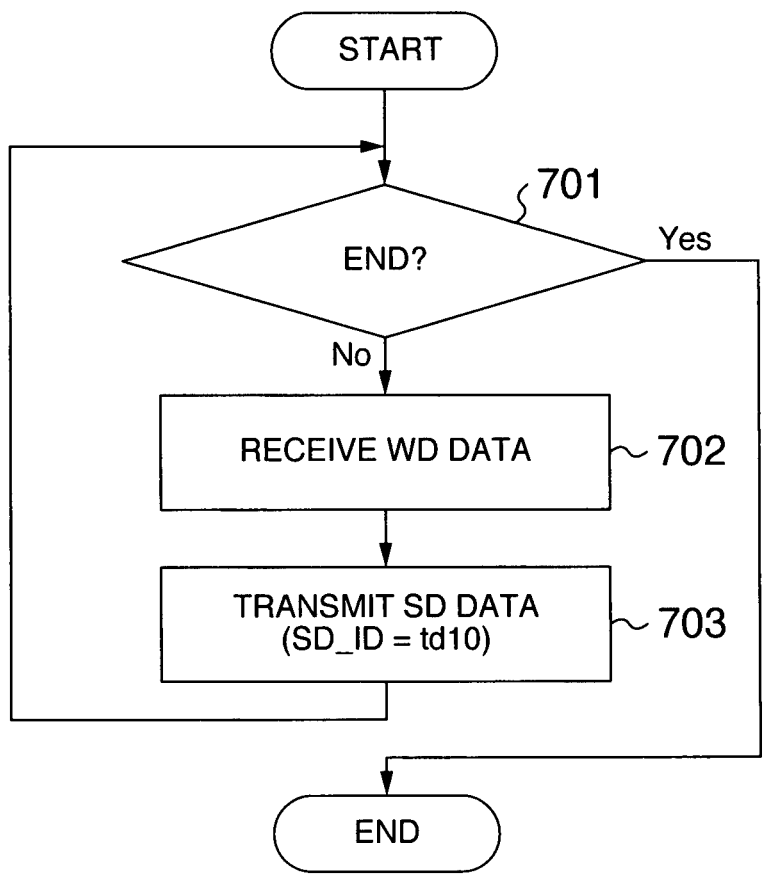
FIG. 6 is a flow chart showing an operation of a wireless repeater.

FIG. 6 is a flow chart showing an operation performed by the wireless repeater 170 when it receives the WD data.

When the wireless repeater 170 is started, it executes step 701 to check whether or not to stop its operation. If the step 701 decides that the operation be stopped, the operation is ended.

If the step 701 decides that the operation be continued, the wireless repeater 170 executes step 702 to receive the WD data transmitted from the wearable device 150.

Next, the wireless repeater 170 executes step 703 to add SD_ID (in this example, SD_ID is "td10") identifying the wireless repeater 170 to the received WD data and transmit it as SD data.

If, for example, the WDDATA01 is received, "WD_ID=wd01, SD_ID=td10, Ps=80, BT=36.2, Ac=210" (SDDATA01) is transmitted as SD data.

In this embodiment, the wireless communication between the WD wireless communication unit 155 of the wearable device 150 and the wireless repeater 170 is contemplated to use IEEE802.15.4, ZigBee. This can reduce a power consumption. Other wireless communications may also be used, such as weak radio wave, short-range radio wave, Bluetooth and IEEE802.11b. As a result, a more versatile system building is possible.

The SD data transmitted by step 703 is received by the data server 100 via the network 140.

Figure 7:
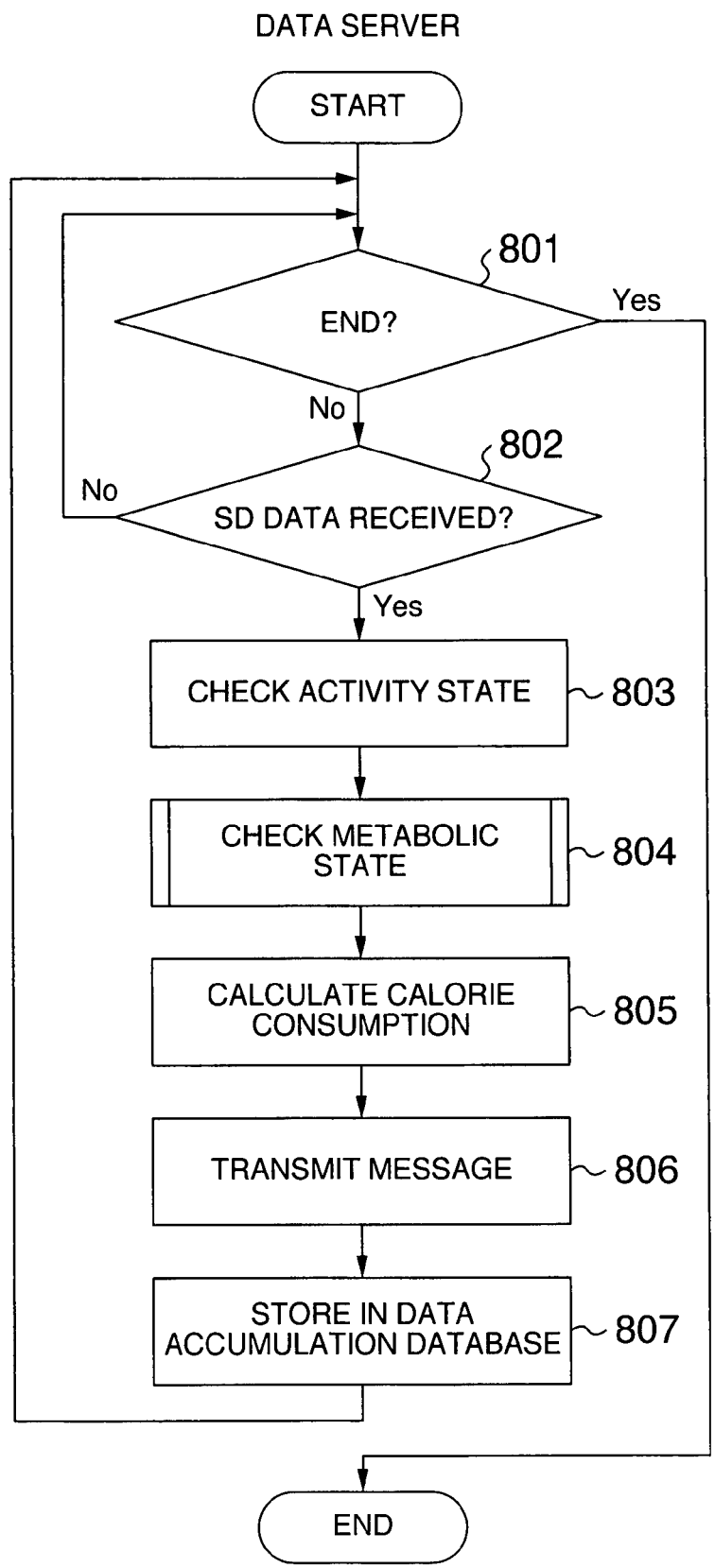
FIG. 7 is a flow chart showing an operation of a data server when it receives data.

FIG. 7 is a flow chart showing an operation performed by the data server 100 when it receives data. First, when the data server 100 is started, the DS control unit 101 executes step 801 to check whether or not the reception operation should be stopped. If the step 801 decides that the operation be stopped, the operation is ended.

If the step 801 decides that the operation be continued, the DS control unit 101 executes step 802 to receive the SD data sent from the wireless repeater 170.

Next, the DS control unit 101 starts the activity state decision unit 105 to execute step 803 that determines the state of physical activity from the SD data received at step 802 by using knowledge of the activity state decision knowledge table 420.

In the case of SDDATA01, for example, the body movement "Ac" is 210, which meets the decision condition of "Ac≥120". So, the state of activity is "active" (activity state ID is "S_AC").

For SD data with "WD_ID=wd01, SD_ID=td10, Ps=71, BT=36.2, Ac=50" (SDDATA02), the body movement "Ac" is 50, which satisfies the decision condition of "Ac<120". So, the state of activity is "resting" (activity state ID is "S_ST").

For SD data with "WD_ID=wd01, SD_ID=td10, Ps=62, BT=35.8, Ac=10" (SDDATA03), the body movement "Ac" is 10, which satisfies the decision condition of "Ac<40". So, if the time, during which the decision condition of "Ac<40" is met, lasts 30 minutes or more (decision condition "L≥30"), the state of activity is "sleeping" (activity state ID is "S_SL").

Although the lasting time for a particular state is set to 30 minutes or more in this example, any other length of time may be used.

As described above, the use of the activity state decision knowledge base makes it possible to determine the activity state—"resting", "active" or "sleeping"—from the biological information collected from the wearable device 150.

Further, the addition of the lasting time to the condition of determining the sleep state can prevent sedentary routine works, such as reading papers and books and operating on a personal computer, from being erroneously determined as sleeping. This makes the decision on the activity state more accurate.

The activity state decision knowledge table 420 determines the activity state from only the body movement Ac. The pulse rate Ps and skin temperature BT may also be used in combination, allowing for more accurate decision of the activity state.

Next, the DS control unit 101 starts the metabolic state decision unit 106 to execute step 804 that determines a metabolic state from the SD data received at step 802.

Figure 8:
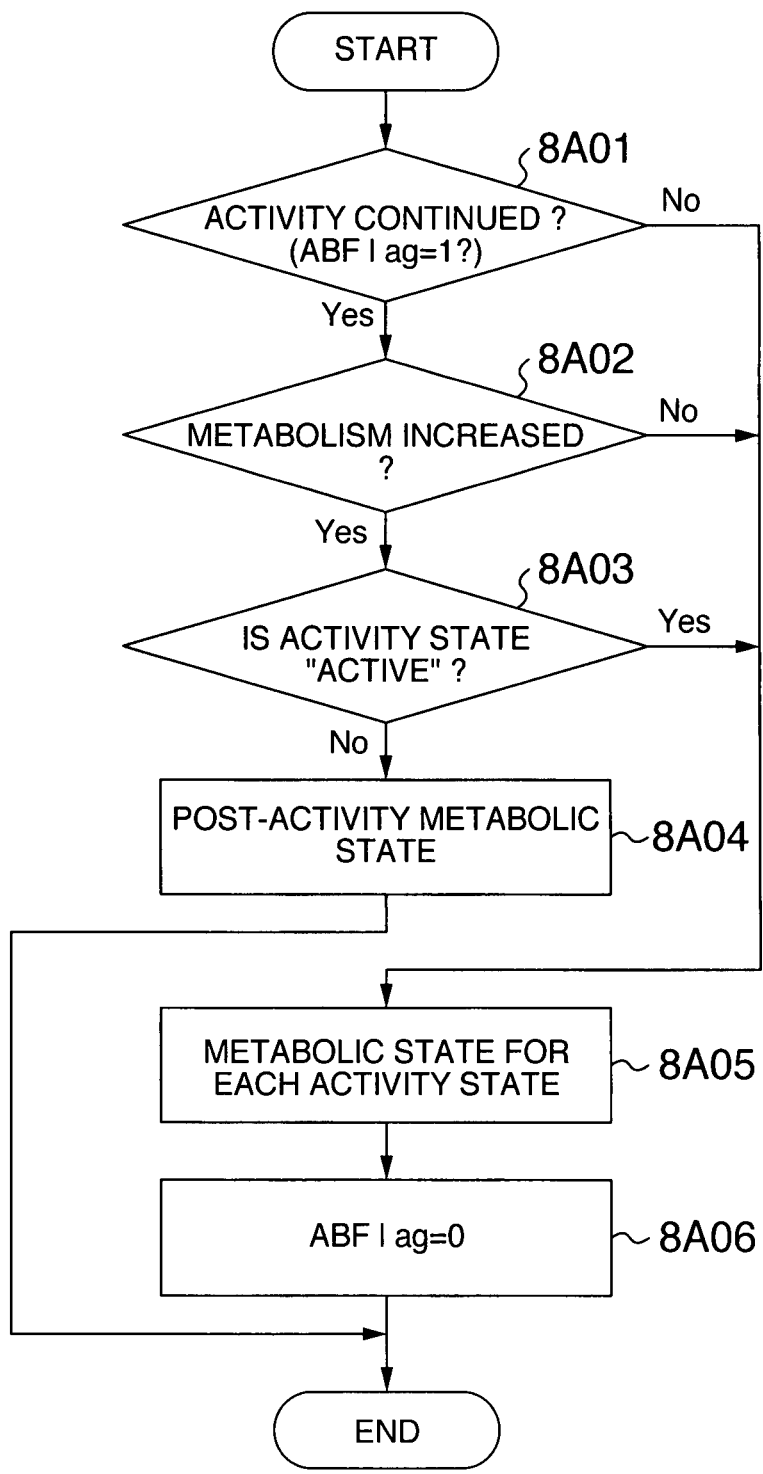
FIG. 8 is a flow chart showing an operation of the data server when it makes a decision on a metabolic state.

FIG. 8 is a flow chart showing an operation of step 804 in making a decision on the metabolic state. First, the metabolic state decision unit 106 executes step 8A01 to decide whether or not a activity state continuation flag "ABFlag=1" indicating that the activity state of interest is continuing is stored in the DS memory 102.

The decision is made of the activity state continuation flag by the following equation 3.

$$ABFlag = \begin{matrix} 1 & (AcT \geq 120) \\ 0 & (AcT < 120) \end{matrix} \qquad \text{Equation 3}$$

where $$AcT = \sum_{t=-10}^{0} Ac(t)$$

If step 8A01 decides that the continuation flag is not set, the metabolic state decision unit 106 executes step 8A05, which determines a metabolic state for each activity state. That is, the step 8A05 determines the metabolism to be in a "sleeping" metabolic state when the activity state is "sleeping", in a "resting" metabolic state when the activity state is "resting", or in an "active" metabolic state when the activity state is "being active". The step 8A05 then stores the determined metabolic state in the DS memory 102.

Following the step 8A05, the metabolic state decision unit 106 executes step 8A06 to initialize (ABFlag=0) the activity state continuation flag ABFlag stored in the DS memory 102.

If the step 8A01 decides that the activity state continues, the metabolic state decision unit 106 executes step 8A02 which decides whether or not the metabolism has increased (metabolism is on the rise) by checking changes in the pulse rate and skin temperature, i.e., a magnitude of difference from the resting state.

More specifically, the decision is made by the following equation 4 using the rest state skin temperature Tstb and the rest state pulse rate Pstb described in the parameter 213 of the user's personal information table 210.

$$BT - Tstb \geq 0.1 \text{ and}$$

$$Ps - Pstb \geq 1.0 \qquad \text{Equation 4}$$

For example, the parameter 213 has Tstb=36.0 and Pstb=71. So, in the case of the user data record 310B stored in the user data history table 310, the skin temperature BT=37.3 and the pulse rate Ps=80, indicating that the skin temperature and the pulse rate are both higher than those during rest. Therefore, this state is determined to be an "ascending metabolic state". However, when only the pulse rate or skin temperature is higher than in the rest state, as in user data record 310D or user data record 310E, the metabolism is not decided as increasing.

As described above, in determining when the metabolism is increasing, combining the skin temperature that changes according to environment and the pulse rate that changes according to the mental state of the user can reduce mental and environmental influences, assuring a decision with higher reliability.

As described above, by checking whether the metabolism is increasing or not only after it is decided from various sensor signals that the activity state is continuing, the state in which the metabolism is increasing in the recovery process following physical movements (post-activity metabolic state) can be determined precisely.

If the step 8A02 decides that the metabolism is not increasing, the metabolic state decision unit 106 executes step 8A05 and step 8A06 and ends this processing.

If the step 8A02 decides that the metabolism is increasing, the metabolic state decision unit 106 executes step 8A03 to check whether the activity state is "active" or not. If the step 8A03 decides that the activity state is "active", the metabolic state decision unit 106 executes step 8A05 and step 8A06 and terminates this processing.

If the step 8A03 decides that the activity state is not active, the metabolic state decision unit 106 executes step 8A04 that determines the metabolism to be in a "post-activity metabolic state" and stores the determined metabolic state in the DS memory 102 before exiting this processing.

After the step 804 is finished, the DS control unit 101 starts the calorie consumption calculating unit 107 to execute step 805 that calculates a calorie consumption by changing the calorie consumption calculating algorithm according to the metabolic state stored in the DS memory 102.

Next, the DS control unit 101 uses the DS communication unit 108 to execute step 807 that transmits message data including the activity state, the metabolic state and the calorie consumption to the wearable device 150 through the repeater 170.

FIG. 11A, 11B, 11C show example screens 1300 of the output unit 160 when the wearable device 150 receives the message data transmitted by step 807.

The example screens 1300 have an area 1301 showing a total of the calorie consumptions in the message data received, an area 1302 showing the activity state, and an area 1303 representing a rising metabolic state.

When the activity state is "resting" and the metabolic state is a "metabolism in rest state", "rest" is displayed in the area 1302, as shown in FIG. 11A.

When the activity state is "active" and the metabolic state is a "metabolism in active state", "active" is displayed in the area 1302 and an increasing metabolism is displayed in the area 1303, as shown in FIG. 11B.

Here, when the activity state returns to the "rest state" but the metabolic state is "post-activity metabolism", "rest" is displayed in the area 1302 and an increasing metabolism is displayed in the area 1303, as shown in FIG. 1C.

By changing the output method on the display according to the metabolic state, the user can easily recognize the metabolic state as it changes in his body. Further, since the state of the post-activity metabolism is output to the display in a manner that is distinguishable from other metabolic state, the user can easily recognize the effect of physical activities even after the physical activities are finished.

Next, the DS control unit 101 executes step 807 which stores in the data accumulating database 112 the SD data received by step 802, the activity state calculated by step 803, the metabolic state calculated by step 804 and the calorie consumption calculated by step 805 along with the date and time the SD data was received and the user ID of a record of the SD data whose WD_ID matches the WD_ID field 215 of the user personal information table 210.

For example, if the SDDATA01 was received at 6:32 on Apr. 2, 2004, the user data record 310A is stored in the user data history table 310.

In this way, all the SD data received are accumulated in the user data history table 310 along with the reception date and time.

Figure 9:
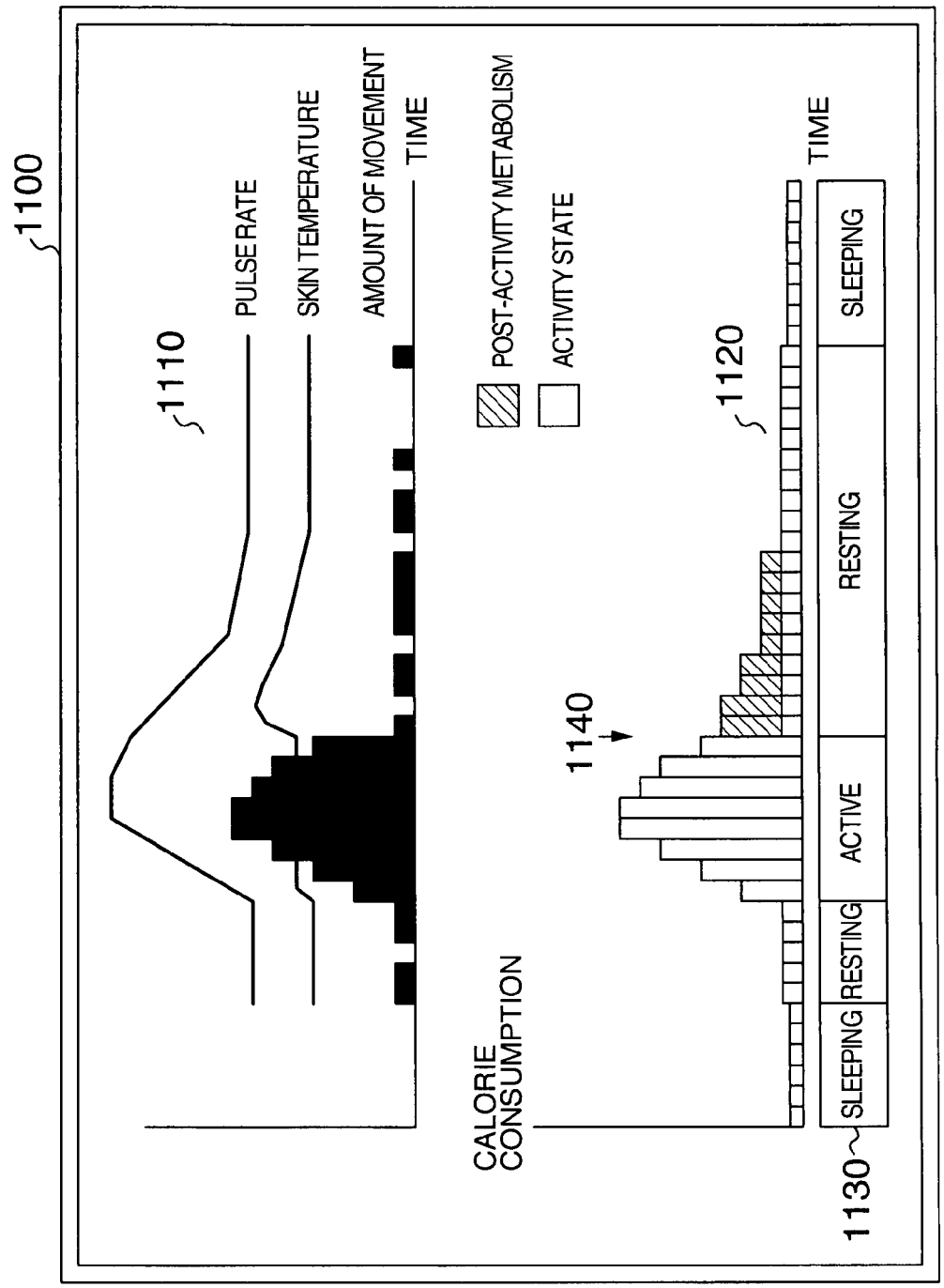
FIG. 9 is an example screen of an input/output terminal.

The accumulated user data can be searched by using the input/output terminal 120. FIG. 9 shows an example screen 1100 when the data accumulating database 112 is accessed using the input/output terminal 120.

The example screen 1100 comprises a data display area 1110, a calorie consumption display area 1120 and an activity state display area 1130. The calorie consumption display area shows a calorie consumption calculated according to the activity state and a calorie consumption by the post-activity metabolism.

As can be seen from FIG. 9, if only the calorie consumption calculated according to the activity state is considered, i.e., the calorie consumption calculating algorithm using METs of reference 1 is used, the algorithm calculates a calorie consumption by the active state metabolism when the activity is in an active state and, when the activity is in a rest state, a calorie consumption by the rest state metabolism. (In FIG. 9, the calorie consumption by the active state metabolism is calculated by using the equation 1 and the amount of body movement Ac, as in the case with the calorie consumption calculation knowledge record 450E.)

Therefore, after the activity state changes from the active state to the rest state, a calorie consumption by the rest state metabolism is calculated.

However, even after the activity state has changed from the active state to the rest state, the metabolism within a human body does not switch instantly from the active state metabolism to the rest state metabolism but rather is considered to progressively decrease. This is also supported by the fact that the pulse rate slowly decreases toward the rest state, as shown at 1110. So, if only the calorie consumption calculated according to the activity state is considered, some errors from the actual calorie consumption will necessarily occur.

On the other hand, as for a calorie consumption calculated based on a post-activity metabolism—the metabolism after the activity state has changed from the active state to the rest state—the calorie consumption is calculated according to the pulse rate. So, the calorie consumption gradually decreases.

In the post-activity metabolic state, since the calorie consumption is calculated using the pulse rate that reflects a metabolism in the user's physical body, it is possible to take into account a metabolism that cannot be calculated from the activity state, which only reflects the metabolism resulting from the body movements. Therefore, in the post-activity metabolic state, the use of the pulse rate in calculating a calorie consumption allows for higher precision in calculation than when the calorie consumption calculation is based on the activity state. By changing the calorie consumption calculation algorithm according to the metabolic state as described above, the calorie consumption can be calculated accurately at all times.

With the output method to the display changed according to the metabolic state, as described above, the user can easily recognize the metabolism in his body. Further, since the state of the post-activity metabolism is output to the display in a manner that is distinguishable from other metabolic states, the user can easily recognize the effects of the body exercise even after the physical activity is ended.

With the above-described metabolic energy monitoring device and system, the state of metabolism in the user's physical body following the body movements can be checked, allowing the calorie consumption to be calculated with high precision.

Further, since the state of post-activity metabolism is output to the display in a manner that is distinguishable from other metabolic states, the user can easily recognize the effects of exercise even after the physical workout.

Therefore, the user can easily and accurately check his or her metabolism in the daily life and use it for health care, enhancement of health and prevention of life-style related diseases.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A metabolic energy monitoring system comprising:
a wearable device adapted to be worn on a human body and having a movement sensor providing movement information indicating a body motion, a temperature sensor providing temperature information indicating an amount of generated heat energy, and a pulse wave sensor providing pulse wave information indicating a pulse rate;
a data server including an activity state decision unit determining a current activity state from a plurality of activity states based on the movement information and the activity state decision knowledge data, a metabolic state decision unit, a calorie consumption calculating unit calculating a calorie consumption value and a database storing activity state decision knowledge data and calorie consumption calculation knowledge data; and
an output unit outputting the calorie consumption value,
the plurality of activity states including a sleeping state, a resting state, and an active state,
the calorie consumption calculation knowledge data including a first calorie consumption calculating algorithm that, upon being selected, calculates the calorie consumption value based on the movement information and a second calorie consumption calculating algorithm that, upon being selected, calculates the calorie consumption value based on the pulse wave information,
the metabolic state decision unit detecting whether there is continuity of the current activity state, determining whether the temperature information and the pulse wave information indicate an ascending metabolic state upon detecting there is continuity of the current activity state, and selecting a current metabolic state from a plurality of metabolic states including a post-activity metabolic state and a metabolic state corresponding to each activity state of the plurality of activity states,
the metabolic state decision unit selecting the post-activity metabolic state upon determining that the temperature information and the pulse wave information indicate the ascending metabolic state and determining that the current activity state is the active state, and
the calorie consumption calculating unit selecting the first calorie consumption calculating algorithm upon the metabolic state decision unit selecting the current metabolic state to be a metabolic state other than the post-activity metabolic state, selecting the second calorie consumption calculating algorithm upon the metabolic state decision unit selecting the current metabolic state to be the post-activity metabolic state, and utilizing the selected calorie consumption calculating algorithm to calculate the calorie consumption value, wherein
the selecting of the second calorie consumption calculating algorithm is based on the post-activity metabolic state being determined as a result of the current activity state being the active state and the temperature information and the pulse wave information indicating the ascending metabolic state, and the ascending metabolic state being determined upon a detection of continuity of the current activity state according to the movement information and the activity state decision knowledge data.

2. A metabolic energy monitoring system according to claim 1, wherein the metabolic state decision unit determines whether the temperature information and the pulse wave information indicate the ascending metabolic state using a rest state skin temperature value and a rest state pulse rate value.

3. A metabolic energy monitoring system according to claim 1, wherein the activity state decision unit determines the activity state by considering the movement information provided over a predetermined duration by the movement sensor.

4. A metabolic energy monitoring system according to claim 1, wherein the output unit outputs a display of the calorie consumption value, and wherein a format of the display when the current metabolic state is selected as the post-activity metabolic state is different than when the current metabolic state is another metabolic state.

5. A metabolic energy monitoring system according to claim 1, wherein the movement sensor is an impact sensor or an acceleration sensor.

6. A metabolic energy monitoring system according to claim 1, wherein the metabolic state decision unit determines that the temperature information and the pulse wave information indicate the ascending metabolic state according to a difference in the temperature information and the pulse wave information used to determine the current metabolic state and the temperature information and the pulse wave information previously provided when the activity state decision unit determined the current activity state to be the resting state.

* * * * *